United States Patent [19]

Salmond

[11] 3,970,676

[45] July 20, 1976

[54] NOVEL PROCESS AND INTERMEDIATE COMPOUNDS USED IS PREPARATION OF -Δ5,7- STEROID DIENES

[75] Inventor: William G. Salmond, Kalamazoo, Mich.

[73] Assignee: The Upjohn Company, Kalamazoo, Mich.

[22] Filed: Oct. 29, 1974

[21] Appl. No.: 518,466

[52] U.S. Cl............................. 260/397.2; 424/238
[51] Int. Cl.²............................................. C07J 9/00
[58] Field of Search................................. 260/397.2

Primary Examiner—Elbert L. Roberts
Attorney, Agent, or Firm—Martin B. Barancik; Roman Saliwanchik

[57] ABSTRACT

A method for preparing the 5,7- steroid diene illustrated below, and intermediates thereof, has been discovered.

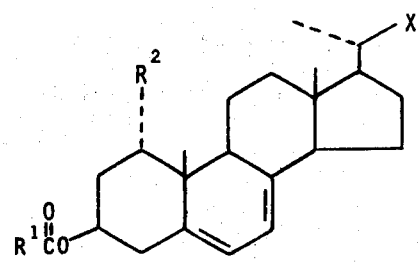

31 Claims, No Drawings

NOVEL PROCESS AND INTERMEDIATE COMPOUNDS USED IS PREPARATION OF -Δ5,7-STEROID DIENES

BRIEF DESCRIPTION OF THE INVENTION

A new method for preparing a 5,7-steroid diene has been discovered. This method comprises a. epimerising a 7β-bromo steroid of the structure

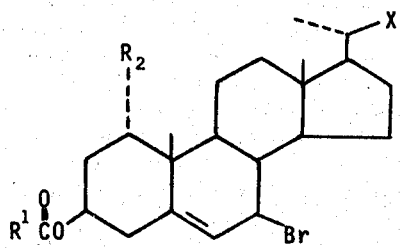

Figure I wherein $R^1$ is selected from alkyl of one to five carbon atoms, inclusive, and

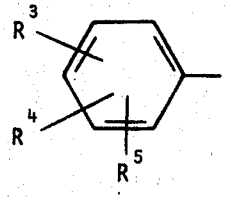

wherein $R^3$, $R^4$ and $R^5$ are the same or different and are selected from the group consisting of hydrogen, alkyl of one to four carbon atoms, inclusive, alkoxy of one to four carbon atoms, inclusive, and halogen.

$R^2$ is selected from the group consisting of hydrogen and

wherein $R^1$ is as defined above;

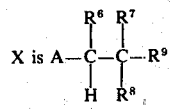

wherein A is selected from the group consisting of —CH$_2$—CH$_2$—, —CH=CH—, and —C≡C—, $R^6$, $R^7$, and $R^8$ are the same or different and are hydrogen or methyl, $R^9$ is selected from the group consisting of hydrogen, hydroxy, and

with the proviso that when $R^9$ is hydrogen, then A is CH$_2$—CH$_2$, $R^6$ is hydrogen, and $R^7$ and $R^8$ are methyl;

when $R^9$ is hydroxy or

and $R^7$ and $R^8$ are hydrogen, then $R^6$ is hydrogen;
when $R^9$ is hydroxy or

$R^7$ is hydrogen or methyl and $R^8$ is methyl, then $R^6$ is hydrogen or methyl;

b. reacting the 7α-bromo compound with Y selenolate wherein Y is

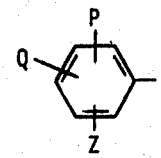

with P, Q, and Z being the same or different and selected from the group consisting of hydrogen, alkyl of one to four carbon atoms, inclusive, alkoxy of one to four carbon atoms, inclusive, and halogen to form the 7β-selenide, c. oxidizing the selenide to form compounds of the group

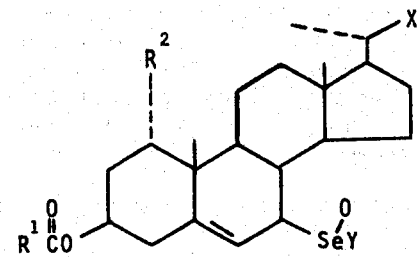

Figure II wherein $R^1$, $R^2$, X and Y are as defined above, d. decomposing the oxidized selenide of Step c to compounds of the group

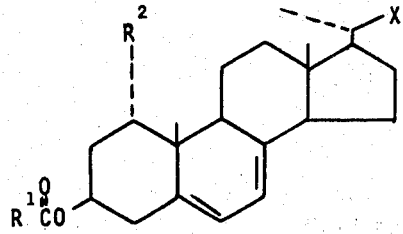

Figure III wherein $R^1$, $R^2$ and X are as defined above.

Another aspect of the invention is epimerizing the 7β-bromo compound of FIG. I to 7α-bromo compounds in the presence of a cyclic ether solvent.

A further aspect of the invention is converting the 7α-bromo compounds of Step a to the 7β-selenides by contacting the bromo compound with Y selenolate wherein Y is defined as above.

A still further aspect of the invention is the oxidizing of the selenide to the compounds of FIG. II.

Another aspect of the invention is the decomposition of compounds of FIG. II to compounds of FIG. III.

An additional aspect of the invention are the compounds

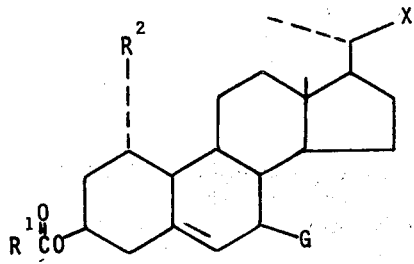

Figure IV where $R^1$, $R^2$ and X are as defined above and G is SeY or

wherein Y is defined as above.

DETAILED DESCRIPTION OF THE INVENTION

The phrase "alkyl of one to six carbon atoms, inclusive", includes methyl, ethyl, propyl, butyl, pentyl, and hexyl and isomers thereof. Illustrative examples of isomers are isopropyl, tert. butyl, neopentyl and 2,3-dimethylbutyl. Expressions of alkyl of lower carbon atom limitations have the same breadth. "Alkoxy" of certain carbon limitations refer to an ether linkage followed by an alkyl chain of the given number of carbon atoms. The term "halogen" includes fluorine, chlorine, bromine and iodine.

The β bromo starting material of this process is prepared through the 7β bromination of the following steroid compounds:

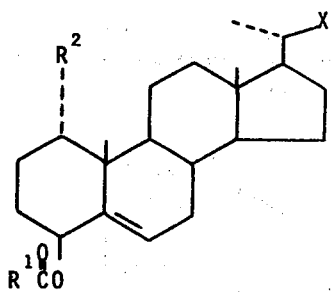

Figure V wherein $R^1$, $R^2$ and X are as defined above.

The bromination is carried out by conventional procedures. A bromine radical is generated from materials such as an N-bromoamide, for example, N-bromosuccinimide, N-bromoacetamide, and dibromantin. This radical reacts with the appropriate steroid in a nonpolar organic solvent such as an alkane, e.g., pentane, hexane, heptane, octane and their isomers, benzene or carbon tetrachloride. Generally, heat is required and temperatures up to the reflux temperature of the system can be employed.

The 7β-brominated steroid, FIG. I, is then epimerized to the α epimer by contact with a dry, inert, aprotic polar organic solvent. By inert is meant not reacting with the steroid nor causing the steroid to react or decompose. The term "aprotic" refers to the absence of an acidic hydrogen. "Polarity" refers to a dipole moment. Examples of such groups of solvents include ketones, ethers, and esters up to about six carbon atoms. Specific solvents which can be employed are acetone, methylethylketone, dioxane 1,4 and 1,3,diethyl ether, tetrahydrofuran, butylacetate, and ethylacetate.

Preferred solvents are cyclic, mono and di ethers of four carbon atoms. Particularly preferred is tetrahydrofuran because of the clean solution and easy workup. A solvent which cannot be used because of undesirable reaction is dimethylformamide. The temperature at which the epimerization takes place is not critical. Any temperature from about 20°C. to about the reflux temperature of the system can be employed. The reaction time period is related to the temperature.

The 7α-bromo steroid prepared above is reacted with Y selenolate to form a 7β-selenide wherein Y is

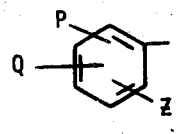

with P, Q and Z being the same or different and selected from the group consisting of hydrogen, alkyl of one to four carbon atoms, inclusive, alkoxy of one to four carbon atoms, inclusive, and halogen. Preferred substituents are electron releasing groups, such as alkoxy, para to the selenium. Particularly preferred is methoxy. Illustrative Y groups are phenyl, o-tolyl, m-xylyl, o-ethoxyphenyl, p-chloro, p-butyl, and n-propoxy. The Y selenolate can be reacted with the steroid in any convenient form, although its presence as the alkali metal salt, for example, sodium or potassium, is preferred. The Y selenolate is easily prepared by art known methods. For example, a solution of sodium phenylselenolate in tetrahydrofuran is produced by allowing a solution of diphenyldiselenide in tetrahydrofuran containing up to about 10% water to react with sodium borohydride. The temperature at which the reaction of the Y selenolate with the steroid occurs is not unduly significant. Temperatures from about −25° to about +60°C. can be used with facility, preferably from about 10° to about 40°C. Any inert organic solvent which dissolves the reactants can be employed, for example, ethers of up to six carbon atoms, inclusive, and aryl groups of six to ten carbon atoms. Examples of such solvents include tetrahydrofuran, diethylether, benzene, toluene and xylene. A preferred solvent is tetrahydrofuran.

The 7β-selenide is then oxidized to compounds of FIG. II. Compounds which carry out this oxidation are ozone, hydrogen peroxide, per acids such as per lower alkanoic alkyl of one to four carbon atoms, inclusive, and lower alkyl peroxides, e.g., tert-butyl peroxide. When using hydrogen peroxide or the lower alkyl peroxide, it is preferred to use catalytic quantities of a transition metal coordinated, i.e., complexed, with 1,3-dicarbonyl compounds. Examples of such transition metals are vanadium and molybdenum. Examples of suitable ligands which can be complexed with the transition metals are 2,5 pentanedione (acac) and acetoacetic ester. When using molybdenum as the metal, oxygen may also be a ligand. If oxygen is a ligand, all the ligands of the complex need not be restricted to oxygen. Additional ligands can be hexamethylphosphorous triamide (HMPA), pyridine, and γ-picoline, for example. Illustrative examples of specific catalysts which can be employed are VO(acac)$_2$, Mo(acac)$_3$, and MoO$_5$.HMPA. A preferred catalyst is MoO$_5$.HMPA. A suitable quantity of catalyst is that amount which significantly reduces the exotherm accompanying the oxidation. By reducing this exotherm, the oxidation occurs at a lower temperature. Therefore, the ensuing decomposition of FIG. II compounds to FIG. III compounds is more easily controlled. Quantities of catalyst employed are from about 0.05 to about 5% weight of the steroid, preferably from about 0.1 to about 1%. When tert. butyl peroxide is employed, a catalyst is required.

The temperature at which the oxidation occurs varies according to the oxidizing agent employed and the presence or absence of a catalyst. The appropriate temperatures are within the skill of the art and can be determined with little effort. For example, oxidation of the selenide with ozone occurs at −60° to −100°, conveniently at −68°C. However, when using hydrogen peroxide, the oxidation occurs readily at −10° to +5°C. When accompanied by a catalyst such as MoO$_5$.HMPA, the hydrogen peroxide oxidation is conveniently carried out at −15°C. When tert. butyl peroxide is used in conjunction with a catalyst, the reaction is conveniently carried out at 20°C.

If allowed to stand at the temperature at which the oxidation is carried out or allowing the temperature to slowly rise, the FIG. II compounds decompose to the desired FIG. III compounds. The time span for the decomposition depends upon the temperature at which the FIG. II compounds are maintained. For example, at −10° to 0°C., the decomposition occurs over a time span of approximately two hours. At lower temperatures, the time is increased. At higher temperatures, the time is decreased; however, care should be taken so that the decomposition remains under control. A preferred temperature at which the decomposition occurs is from about −20° to about 0°C., more preferably about −5° to about 0°C.

Following are examples illustrative of the inventive scope. These examples are not intended to restrict the scope of the invention but to exemplify the nature of the invention. All R$_f$ values were obtained using silica gel.

EXAMPLE 1

7β-Phenylseleno-cholesteryl benzoate

Diphenyl diselenide (1.60 g.) is dissolved in 20 ml. tetrahydrofuran containing five drops of water. Sodium borohydride (ca. 100 mgs.) is added portionwise until the solution becomes colorless, i.e., until reduction to sodium phenyl selenolate is complete. During this addition effervescence occurs and the temperature rises to ca. 45°. At this point 7α-bromocholesteryl benzoate (5.70 g.) dissolved in 40 ml. dry tetrahydrofuran is added all at once. An immediate white suspension of sodium bromide is formed. Tlc analysis of the solution within ca. 2 minutes indicates that the reaction is complete. The reaction mixture is now poured into water and extracted with benzene. The extracts are dried and evaporated. The residue is dissolved in 25 ml. acetone and left at 0° for a number of hours. The crystalline product is then filtered off to give the desired product (5.3 g.) m.p. 121°–122°.

NMR (CDCl$_3$): δ 0.51s(3H); 0.73s(3H); 3.47 b.d.(1H); 4.80 b.m.(1H); 5.56m(1H); 7.11–7.67m(8H); 7.21–8.02m(2H); R$_f$: 10% ethyl acetate/Skellysolve B -- 0.62

EXAMPLE 2

7-Dehydrocholesteryl benzoate

To a solution of the selenide prepared in Example 1, (646 mgs.) in 10 ml. tetrahydrofuran at −5°, is added 0.043 ml. of 60% hydrogen peroxide. The temperature is allowed to rise slowly to 0° and after two hours, methanol is added to precipitate the product. 7-dehydrocholesteryl benzoate, m.p. 140°–142°. The structure is confirmed by comparison with an authentic sample.

EXAMPLE 3

7β-Phenylseleno-cholesteryl acetate

Cholesteryl acetate (8.58 g.) is dissolved at room temperature in a mixture of benzene (60 ml.) and hexane (60 ml.). Dibromantin (3.2 g.) is added. The mixture is stirred under nitrogen and brought to reflux during 5 minutes. The boiling is continued for 5 minutes and the temperature allowed to subside during 10 minutes to 45°C. at which time the mixture is cooled in an ice bath during ca. 5 minutes to 0°C. before being filtered and evaporated to dryness at room temperature. The residue is dissolved in 100 ml. dry tetrahydrofuran and allowed to stand for 2½ hours, during which time the epimerization of the 7β- to the 7α-bromide takes place. At this point the solution is boiled for ca. two minutes to ensure equilibration of the isomers and then allowed to cool to room temperature. In the meantime, a solution of sodium phenylselenolate is prepared from 3.2 g. diphenyldiselenide in 100 ml. tetrahydrofuran containing 6 ml. water and portionwise addition of sodium borohydride.

The solution of the bromide is now added all at once and after 15 minutes the reaction mixture is poured into water and extracted with Skellysolve B. The extracts are washed with water, dried and evaporated to yield an oil of the desired selenide.

NMR: (CDCl$_3$): 0.47s(3H); 0.70s(3H), 1.98s(3H); 3.42b.d.(1H); 4.5b.m.(1H); 5.50m(1H); 7.12–7.72m(5H). R$_f$: 10% ethyl acetate/Skellysolve B -- 0.37.

EXAMPLE 4

In a manner similar to that described in Example 2, the selenide of Example 3 is oxidized and then decomposed to yield 7-dehydrocholesteryl acetate.

EXAMPLE 5.

25-Acetoxy-7β-phenylseleno-cholesteryl acetate

Dibromantin (0.16 g.) is added to a solution of 25-acetoxycholesteryl acetate (0.49 g.) in a mixture of benzene (3 ml.) and hexane (3 ml.) at reflux under nitrogen and the reflux continued for 5 minutes before cooling quickly to 0°C. The mixture is filtered and concentrated to an oil at 20°C., which is dissolved in 5 ml. acetone and allowed to stand in the dark at room temperature for 3½ hours to allow epimerization of the 7β to 7α-bromide. In the meantime, a solution of sodium phenylselenolate in 5 ml. tetrahydrofuran is prepared from 0.16 g. diphenyl diselenide as described in Examples 1 and 3. The acetone solution of the 7α-bromide is added to the solution of the organo-selenium reagent and after 15 minutes the mixture is poured into water and extracted with Skellysolve B. The extracts are washed with water, dried and evaporated to yield an oil of the desired selenide.

NMR: (CDCl$_3$): δ 0.47s(3H); 0.72s(3H); 1.42s(6H); 1.95s(3H); 2.00s(3H); 3.42b.d.(1H); 4.50b.m.(1H); 5.50m(1H); 7.12–7.63b.m.(5H). R$_f$: 20% ethyl acetate/Skelly B -- 0.46.

EXAMPLE 6

25-Acetoxy-7-dehydrocholesteryl acetate

The oil obtained from Example 5 is dissolved in 5 ml. tetrahydrofuran and cooled to −5°C. Three drops of 90% hydrogen peroxide are added. After 30minutes at 0°C., the mixture is poured into water and extracted with Skellysolve B. The extracts are washed with water, dried and evaporated to yield an oil which is chromatographed on silica, eluting with 1% ethyl acetate in Skellysolve B. The fractions containing the desired product are combined, evaporated and the residue crystallized from acetone-acetonitrile mixture.

U.V (EtOH) 271 n.m. (11,580); 281 (12,151); 294 (7,007). NMR: (CDCl$_3$): δ 0.63s(3H); 0.95s(3H); 1.43s(6H); 1.95s(3H); 2.03s(3H); 4.67b.m.(1H); 5.50 AB system J=6Hz(2H). R$_f$: 20% ethyl acetate/Skellysolve B -- 0.48

EXAMPLE 7

1α-Acetoxy-7β-phenylseleno-cholesteryl acetate

In a fashion analogous to that described in Example 5, 1α-acetoxy cholesteryl acetate is converted into the 7β-phenylseleno compound as an oil.

NMR. (CDCl$_3$): δ 0.47a(3H); 0.70s(3H); 0.81s; 0.91s; 2.00s(6H); 3.43m(1H); 4.95m(2H); 5.63m(1H); 7.13 –7.73m(5H). R$_f$: 20% ethyl acetate/Skellysolve B -- 0.43

EXAMPLE 8

1α-Acetoxy-7-dehydrocholesteryl acetate

In a fashion exactly analogous to that described in Example 6, the oil from Example 7 is oxidized and thereby converted into 1α-acetoxy-7-dehydrocholesteryl acetate, m.p. 114°–115° ex chloroform/acetonitrile.

NMR (CDCl$_3$): δ 0.62s(3H); 0.82s(3H); 0.90; 1.00; 2.00s(3H); 2.06s(3H); 5.00m(1H); 5.42m(1H); 5.69 AB system J=8Hz(2H). U.V. (EtOH): 271 n.m. (11,511), 282 (12,354), 293 (7,270). R$_f$: 20% ethyl acetate/Skellysolve B - 0.44

EXAMPLE 9

A solution of 7β-phenylseleno-cholesteryl benzoate (1.29 g.) in tetrahydrofuran (10 ml.) containing triethylamine (0.6 ml.) is cooled to −7° and 30% hydrogen peroxide (0.3 ml.) is added. After a slight exotherm due to the addition, MoO$_5$·(Me$_2$N)$_3$P–O(10 mgs.) in 1 ml. tetrahydrofuran is added. After 20minutes the reaction mixture is poured into water and worked up using conventional procedures to yield 7-dehydrocholesteryl benzoate.

EXAMPLE 10

The syntheses of Example 1-9 are carried out on compounds wherein R$^1$ is one of the following groups:

R$^1$ ethyl
propyl
isopropyl
butyl
tert. butyl
pentyl
neopentyl
o-tolyl
2,4-xylyl
p-ethoxyphenyl
p-isobutylphenyl
p-cholorophenyl
m-bromophenyl
o-fluorophenyl
p-chloro-o-tolyl 2-methyl-4-bromophenyl Similar results as in Examples 1-8 are obtained with these R$^1$ substituted compounds.

EXAMPLE 11

The syntheses of Examples 1–10 are carried out on compounds wherein R$^2$ is defined as

with R$^1$ illustratively exemplified as in Example 9. Similar results as in Examples 1–9 are obtained with these R$^2$ substituted compounds,

EXAMPLE 12

The syntheses of Examples 1–11 are carried out on compounds where X is the following:

| A | R$^6$ | R$^7$ | R$^8$ | R$^9$ |
|---|---|---|---|---|
| —CH$_2$—CH$_2$— | H | CH$_3$ | CH$_3$ | H |
| —CH$_2$—CH$_2$— | H | H | H | OH |
| —C≡C— | H | H | H | *R$^1$C(=O)—O |
| —CH=CH— | H | H | H | OH |
| —CH$_2$—CH$_2$— | CH$_3$ | H | CH$_3$ | OH |
| —CH=CH— | H | CH$_3$ | CH$_3$ | *R$^1$C(=O)—O |
| —C≡C— | H | H | CH$_3$ | OH |

*R$^1$ illustratively exemplified as in Example 9. Similar results as in Examples 1–10 are obtained with these X substituted compounds.

EXAMPLE 13

The 7α-bromo steroid is reacted with Y-selenolate wherein the Y is the following:

Y o-tolyl
2,4-xylyl
p-ethoxyphenyl
m-isobutylphenyl
p-chlorophenyl
m-bromophenyl
o-fluorophenyl
p-chloro-o-tolyl
2-methyl-4bromophenyl Similar selenides as obtained previously are prepared with these compounds.

I claim:
1. A process for preparing compounds of the formula

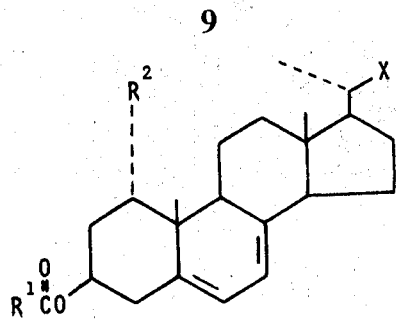

wherein $R^1$ is selected from alkyl of one to five carbon atoms, inclusive, and

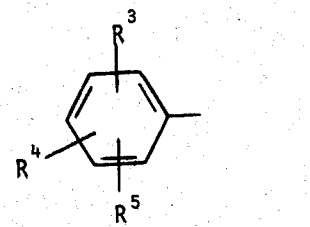

wherein $R^3$, $R^4$, and $R^5$ are the same or different and are selected from the group consisting of hydrogen, alkyl of one to four carbon atoms, inclusive, alkoxy of one to four carbon atoms, inclusive, and halogen;
$R^2$ is selected from the group consisting of hydrogen and

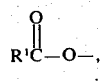

$R^1$ defined as above;

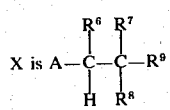

wherein A is $-CH_2-CH_2-$,
$R^6$, $R^7$, $R^8$ are the same or different and are hydrogen or methyl;
$R^9$ is selected from the group consisting of hydrogen, hydroxy, and

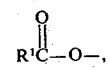

$R^1$ as defined above, with the proviso that when $R^9$ is hydrogen, A is $-CH_2-CH_2$, $R^6$ is hydrogen and $R^7$ and $R^8$ are methyl; and
when $R^9$ is hydroxy or

$R^1$ defined as above, and $R^7$ and $R^8$ are hydrogen, then $R^6$ is hydrogen;
when $R^9$ is hydroxy or

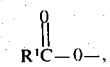

$R^7$ is hydrogen or methyl, and $R^8$ is methyl, then $R^6$ is hydrogen or methyl, which comprises
a. epimerizing a 7β-bromo steroid of the formula

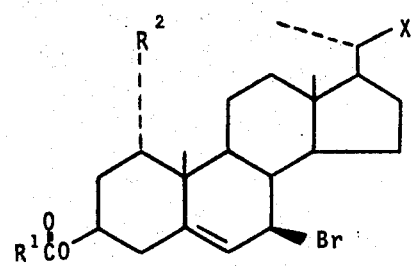

wherein $R^1$, $R^2$ and X are defined as above, to the 7α-bromo compound,
b. reacting the 7α-bromo compound with Y selenolate wherein Y is

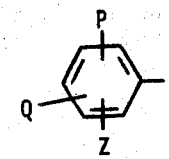

with P, Q, and Z being the same or different and selected from the group consisting of hydrogen, alkyl of one to four carbon atoms, inclusive, alkoxy of one to four carbon atoms, inclusive, and halogen to form the 7β-selenide,
c. oxidizing the 7β-selenide to form compounds of the formula

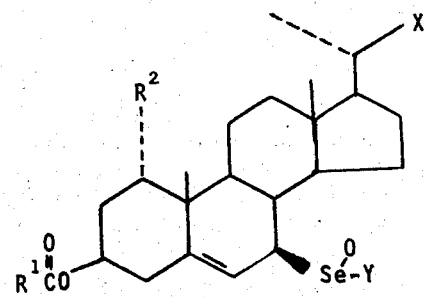

wherein $R^1$, $R^2$, X and Y are as defined above,
d. decomposing the oxidized selenide of Step c to form a compound of the preamble.

2. A process in accordance with claim 1 wherein the epimerization is carried out in dry, aprotic, inert, polar organic solvent.

3. A process in accordance with claim 1 wherein the 7α-bromo compound is reacted with sodium or potassium p-methoxyphenylselenolate.

4. A process in accordance with claim 1 wherein hydrogen peroxide is used to oxidize the selenide.

5. A process in accordance with claim 1 wherein the decomposition occurs at about −20° to about 0°C.

6. A process in accordance with claim 1 wherein

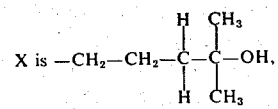

$R^1$ is methyl, $R^2$ is hydrogen and the Y selenolate is sodium p-methoxyphenylselenolate.

7. A process in accordance with claim 2 wherein the epimerization solvent is tetrahydrofuran.

8. A process in accordance with claim 6 wherein the epimerization solvent is tetrahydrofuran.

9. A process in accordance with claim 3 wherein

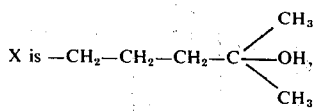

$R^1$ is methyl and $R^2$ is hydrogen.

10. A process in acccordance with claim 4 wherein a transition metal coordination compound is employed in catalytic quantities sufficient to significantly reduce the exotherm accompanying the oxidation.

11. A process in accordance with claim 6 wherein hydrogen peroxide is used to oxidize the selenide.

12. A process in accordance with claim 6 wherein the decomposition occurs at about −20° to about 0°C.

13. A process for epimerizing a 7β-bromo steroid of formula

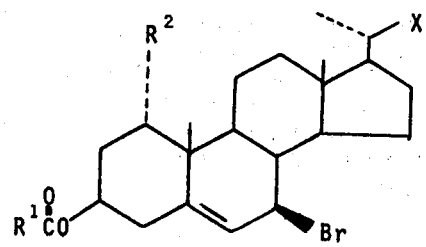

wherein $R^1$, $R^2$ and X are defined as in claim 1 which comprises contacting the above steroid with a cyclic, mono or di ether solvent of four carbon atoms.

14. A process in accordance with claim 13 wherein the cyclic ether is selected from tetrahydrofuran or 1,4 dioxane.

15. A process in accordance with claim 14 wherein the cyclic ether is tetrahydrofuran.

16. A process for preparing compounds of the formula

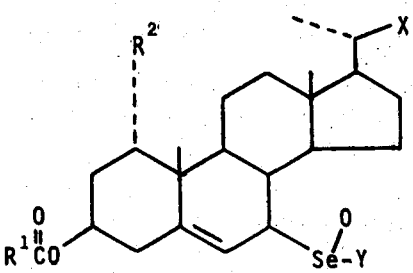

wherein $R^1$, $R^2$ and X are defined as in claim 1 which comprises reacting a 7α-bromo steroid of the same formula with a Y selenolate wherein Y is defined as in claim 1.

17. A process in accordance with claim 16 wherein the Y selenolate is an alkali metal selenolate.

18. A process in accordance with claim 17 wherein the alkali metal is sodium or potassium.

19. A process in accordance with claim 18 wherein Y is p-methoxyphenyl.

20. A process for preparing compounds of the formula

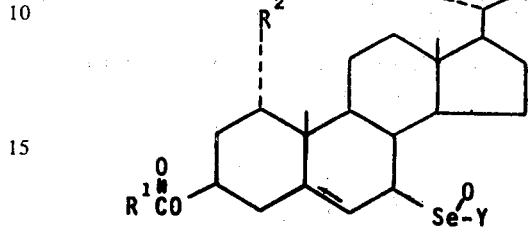

wherein $R^1$, $R^2$, X and Y are defined as in claim 1 which comprises oxidizing the corresponding selenide.

21. A process in accordance with claim 20 wherein hydrogen peroxide is the oxidizing agent.

22. A process in accordance with claim 21 wherein a transition metal coordination compound is employed in catalytic quantities sufficient to significantly reduce the exotherm accompanying the oxidation.

23. A process in accordance with claim 20 wherein the oxidizing agent is tert.butyl peroxide and a transition metal coordination compound is employed in catalytic quantities sufficient to cause reaction to occur.

24. A process for preparing compounds of the formula

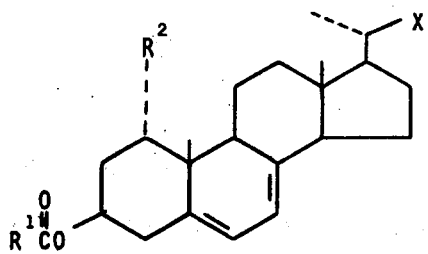

which comprises decomposing compounds of the formula

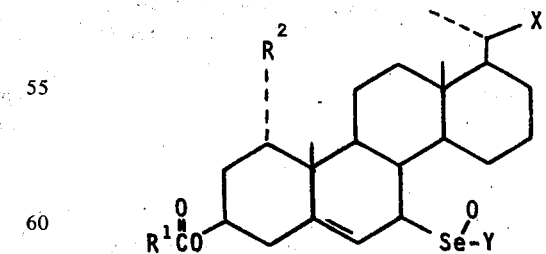

wherein $R^1$, $R^2$, X and Y are defined as in claim 1.

25. A process in accordance with claim 24 wherein the temperature is from about −20° to about 0°C.

26. A process in accordance with claim 24 wherein $R^1$ is methyl, $R^2$ is hydrogen, X is 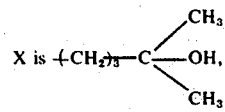

Y is paramethoxyphenyl.

27. A process in accordance with claim 20 wherein $R^1$ is methyl, $R^2$, X and Y are defined as in claim 1.

28. A process in accordance with claim 16 wherein $R^1$ is methyl, $R^2$, X and Y are defined as in claim 1.

29. A process in accordance with claim 13 wherein $R^1$ is methyl, $R^2$, X and Y are defined as in claim 1.

30. Compounds of the formula

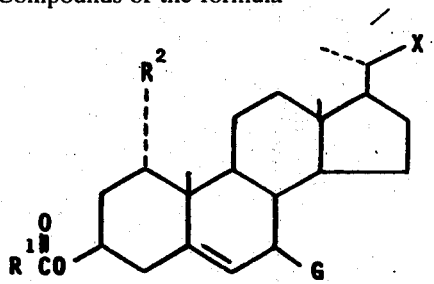

wherein $R^1$, $R^2$ and X are defined in claim 1 and G is SeY or

where Y is defined as in claim 1.

31. Compounds in accordance with claim 30 wherein Y is phenyl or paramethoxyphenyl, X is 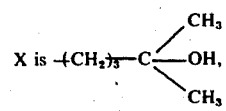

$R^1$ is methyl and $R^2$ is hydrogen.

* * * * *

UNITED STATES PATENT AND TRADEMARK OFFICE
CERTIFICATE OF CORRECTION

PATENT NO. : 3,970,676

DATED : July 20, 1976

INVENTOR(S) : William G. Salmond

It is certified that error appears in the above—identified patent and that said Letters Patent is hereby corrected as shown below:

Front Page [54]; change "IS" to --IN--.

Column 1, line 2; change "Is" to --In--.

Column 5, line 7; change "MoO$_5$.HMPA" to --MoO$_5$·HMPA--.

Column 5, lines 7-8; change "MoO$_5$.HMPA" to --MoO$_5$·HMPA--.

Column 5, lines 26-27; change "MoO$_5$.HMPA" to --MoO$_5$·HMPA--.

Column 6, line 66; change "7βto" to --7β- to--.

Column 7, line 17; change "30minutes" to --thirty minutes--.

Column 7, line 25; change "U.V " to --U.V.--.

Column 7, line 61; change "20minutes" to --twenty minutes--.

Column 8, line 17; change "p-chloro-o-tolyl 2-methyl-4-bromophenyl" to
--p-chloro-o-tolyl
2-methyl-4-bromophenyl--.

Column 8, line 64; change "4bromophenyl" to --4-bromophenyl--.

UNITED STATES PATENT AND TRADEMARK OFFICE
CERTIFICATE OF CORRECTION

PATENT NO. : 3,970,676

DATED : July 20, 1976

INVENTOR(S) : William G. Salmond

It is certified that error appears in the above—identified patent and that said Letters Patent is hereby corrected as shown below:

Column 11, line 42; change "four carbon" to --four ring carbon--.

Column 13, lines 16-18; change "[structure]" to --[structure]--.

Column 14, line 6; change "are defined" to --are as defined--.

Signed and Sealed this

Fifth Day of August 1980

[SEAL]

Attest:

SIDNEY A. DIAMOND

Attesting Officer

Commissioner of Patents and Trademark